(12) United States Patent
Kleinfeld

(10) Patent No.: US 6,444,432 B1
(45) Date of Patent: Sep. 3, 2002

(54) METHOD OF DETECTION OF CARDIAC ISCHEMIA USING FATTY ACID BINDING PROTEIN

(76) Inventor: Alan M. Kleinfeld, 6777 Via Estrada, La Jolla, CA (US) 92037

( * ) Notice: Subject to any disclaimer, the term of this patent is extended or adjusted under 35 U.S.C. 154(b) by 0 days.

(21) Appl. No.: 09/445,499
(22) PCT Filed: Jun. 13, 1997
(86) PCT No.: PCT/US97/10400
§ 371 (c)(1),
(2), (4) Date: Dec. 8, 1999
(87) PCT Pub. No.: WO98/57171
PCT Pub. Date: Dec. 17, 1998

(51) Int. Cl.[7] ............................................. G01N 33/353
(52) U.S. Cl. .......................... 435/7.8; 436/172; 436/518
(58) Field of Search ........................ 435/7.8; 436/518, 436/815, 172

(56) References Cited

U.S. PATENT DOCUMENTS

| 5,449,607 A | 9/1995 | Wilton |
| 5,470,714 A | * 11/1995 | Kleinfeld ..................... 435/7.8 |
| 5,604,105 A | 2/1997 | Jackowski |

FOREIGN PATENT DOCUMENTS

| SU | 1270706 A1 | 9/1981 |
| WO | 91/09310 | * 6/1991 |

OTHER PUBLICATIONS

Ruben, Sandhya MD et al, Journal of American College of Nutrition, vol. 16(1), pp. 85–87, 1997, Serum level of unbound free fatty acids II: The Effect of Intralipid administration in premature Infants.*
Patel, Mahesh N, MD et al, Journal of American College of Nutrition, vol. 16(1), pp. 81–84, 1997, Serum levels of Unbound free fatty acidsl: Normative data in term newborn Infants.*
Samanta, A et al , Journal of Lipid Mediators, vol. 1 (1989), pp. 243–255.*
Ace Current Journal Review May/Jun. 1996, vol. 5(3), p86–89, Ford et al.*

(List continued on next page.)

*Primary Examiner*—Lynette R. F. Smith
*Assistant Examiner*—Ginny Allen Portner
(74) *Attorney, Agent, or Firm*—Knobbe, Martens, Olson & Bear, LLP

(57) ABSTRACT

A method of detecting cardiac ischemia by detecting elevated levels of serum free fatty acids in serum unbound to serum albumin ($FFA_u$) compared to an average $FAA_u$ level in individuals without cardiac ischemia, wherein the detection method uses a free fatty acid binding protein derivatized with a fluorescent moiety, is disclosed.

8 Claims, 3 Drawing Sheets

OTHER PUBLICATIONS

Kleinfeld, et al., The American Journal of Cardiology, vol. 78 No. 12 Dec. 15, 1996;Increases in Serum Unbound Free Fatty Acid Levels Following Coronary Angioplasty;pp. 1350–1354.

Peuhkurinen, et al.; Carduiovascular Research 1991; 25: pp. 158–163; Changes in myocardial energy metabolism in elective coronary angioplasty.

T. Victor, et al.; Journal of Molecular and Cellular Cardiology; vol. 16, No. 8, Aug. 1984; pp. 709–721; Myocardial Tissue Free Fatty Acids.

Samanta, et al.; Free Radical Research Communications; vol. 7, No. 2, pp. 73–82; 1989; Free Radical Scavenging by Myocardial Fatty Acid Binding Protein.

Hoyan, S. She, et al.;Biochem J.; 1994; vol. 298, pp. 23–29; The Substrate Specificities of four different lysophospholipases as determined by a novel fluorescence assay.

Glatz, et al.; BR Heart J.; 1994; vol. 71; pp. 135–140; Fatty–acid–binding protein as a plasma marker for the estimation of myocardial infarct size in humans.

Richieri, et al.; The Journal of Biological Chemistry; vol. 269, No. 39, pp. 23918–23930; 1994; Equilibrium Constants for the Biding of Fatty Acids with Fatty Acid–Binding Proteins from Adipocyte, Intestine, Heart, and Liver Measured with the Fluorescent probe ADIFAB*.

Richieri, et al.; Journal of Lipid Research; vol. 36 No. 2 1995; Unbound free fatty acid levels in human serum pp. 229–240, Feb. 1995.

Richieri, et al.; The Journal of Biological Chemistry; vol. 271, No. 19, May 10, 1996; pp. 11291–11300; Kinetics of Fatty Acid Interactions with Fatty Acid Binding Proteins from Adipolcyte, Heart and Intestine*.

Richieri, et al.; The Journal of Biological Chemistry; vol. 271, No. 49; Dec. 6, 1996; pp. 31068–31074; Thermodynamic and Kinetic Properties of Fatt Acid Interactions with Rat Liver Fatty Acid–binding Protein*.

* cited by examiner

METHOD OF DETECTION OF CARDIAC ISCHEMIA USING FATTY ACID BINDING PROTEIN

This application claims priority under 35 U.S.C. §371 to PCTUS97/10400, filed Jun. 13, 1997.

STATEMENT OF GOVERNMENT RIGHTS

This invention was made with United States government support under Grants GM44171 and GM46931, awarded by the National Institutes of Health. The government of the United States of America has certain rights in the invention.

BACKGROUND OF THE INVENTION

1. Field of the Invention

This invention relates to diagnosis of heart disease, and specifically relates to diagnosis of cardiac ischemia by detecting levels of free fatty acids in serum using a fluorescently-modified free fatty acid binding protein.

2. Description of the Prior Art

Ischemic heart disease affects millions of people worldwide, often leading to sudden death by acute myocardial infarction. Cardiac ischemia is often associated with chest pain (angina pectoris), generally caused by atherosclerosis, but asymptomatic individuals can also be at high risk because of hypertension, high serum cholesterol levels or family history. Myocardial ischemia occurs when blood flow to the heart is restricted or oxygen to heart muscle is compromised (hypoxia). Ischemia and hypoxia can lead to myocardial infarction, during which cardiac tissue is damaged resulting in abnormal cardiac muscle metabolism and contractions.

Diagnostic procedures for heart disease often assess the extent of cardiac tissue damage after symptoms are detected. Then, the disease may have progressed to an extent where AMI is imminent or has occurred. Moreover, about 25% of myocardial infarction (MI) patients display atypical symptoms resulting in misdiagnosis and discharge of about 5% of MI patients (Mair J. et al., *Clin. Chem.* 41:1266–1272, 1995; Newby L. K. et al., *Clin. Chem.* 41:1263–1265, 1995). Electrocardiography (ECG) monitoring of patients for MI detects the condition in only about half of the patients (Mair J. et al., *Clin. Chem.* 41:1266–1272, 1995).

ECG and currently available diagnostic blood tests are often not effective for detecting ischemia because they are designed to monitor infarction-associated tissue damage. Angina symptoms are often confirmed by ECG monitoring during treadmill exercise stress when the patient seeks treatment, but the test has a false negative rate of about 15%. Furthermore, exercise stress testing is usually too expensive and time consuming to be used to screen asymptomatic patients. Thus, a sensitive and reliable diagnostic test is needed for diagnosis of cardiac ischemia, especially for high-risk individuals.

Long-chain free fatty acids (FFA) are essential to normal physiological functions (e.g., as energy sources and cellular activity modulators). Levels of FFA in the serum that exceed the normal range found in serum of healthy individuals are indicative of certain patho-physiological states (Richieri, G. V. & Kleinfeld, A. M., *J. Lipid Res.*, 1995, 36:229–240; Kleinfeld, A. M. et al., 1996, *Am. J. Cardiol*, 78:1350–1354). For example, impaired fatty acid metabolism occurs in individuals with diabetes mellitus, hyperlipidemia and associated with acute myocardial ischemia and/or infarction (Takeishi Y. et al., *Nucl. Med. Commun.*, 1996, 17(8):675–680; Opie, L. H., *Am. J. Cardiol.* 1975, 36:938–953; Katz, A. M. et al., *Circulation*, 1981, 48:1–16; Hochachka, P. W., *Science*, 1986, 231:234–241; Oliver M. F. & Opie, L. H., *Lancet*, 1994, 343:155–158). Myocardial FFA metabolism has also been used to evaluate cardiac function, for example, in patients with hypertensive-diabetic cardiomyopathy, cyanotic congenital heart disease and after coronary thrombolysis (Shimonagata, T. et al., *Diabetes Care*, 1996, 19(8):887–891; Kondo, C. et al., *J. Nucl. Cardiol.*, 1996, 3(1):30–36; Franken, P. R. et al., 1994, *J. Nucl. Med.* 35(11):1758–1765). Typically, tomography imaging has been used to assess myocardial viability and cardiac disease conditions by monitoring myocardial flow tracers (e.g., thallium-201) and uptake of fatty acid analogs (e.g., $^{123}$I-β-methylliodophenylpentadecanoic acid (BMIPP))(reviewed in Franken, P. R. et al., *Acta Cardiol.*, 1996, 51(6):501–514).

Amounts of cholesterol, FFA and lipoproteins in serum have been used as indicators of risk of heart disease. Amounts of phospholipids in cardiac muscle after myocardial infarct can be determined indirectly by measuring blood levels of cholesterol, FFA and β-lipoproteins and then using a mathematical formula to calculate the phospholipid content (Soviet Union Pat. No. 1,270,706). FFA content was measured photo-electro-colorimetrically by forming insoluble complexes with a copper reagent.

Serum FFA is mostly bound to albumin but a significant minority is unbound ($FAA_u$) and soluble in the aqueous phase. Concentrations of $FAA_u$ can measured using a method in which a fluorescently-labeled fatty acid binding protein (FABP) binds to the $FFA_u$ and thereby exhibits a fluorescence different from that exhibited when no FFA is bound (U.S. Pat. No. 5,470,714; PCT Pat. App. WO 91/09310; PCT Pat. App. No. WO 94/06014). The concentration of $FFA_u$ is obtained from the measured fluorescence difference. One such fluorescently-labeled fatty acid binding protein suitable for measuring $FFA_u$ concentrations is rat intestinal FABP derivatized at the Lys-27 residue with acrylodan, referred to as ADIFAB. Using ADIFAB and this method, it was shown that $FFA_u$ levels in serum samples from healthy donors were tightly regulated having a mean value of 7.5±2.5 nM (Richieri, G. V. & Kleinfeld, A. M., *J. Lipid Res.*, 1995, 36:229–240; Richieri, G. V. et al., *J. Biol. Chem.*, 1992, 267:23495–23501).

Current diagnostic methods do not measure serum $FFA_u$ levels but, instead, monitor FFA metabolism relative to abnormal cardiac conditions. These methods generally involve injecting radioactive compounds which are then detected in the patient using tomography imaging (Franken, P. R. et al., *Acta Cardiol.*, 1996, 51(6):501–514; Takeishi, Y. et al., *Nucl. Med. Commun.*, 1996, 17(8):675–680; Shimonagata, T. et al., *Diabetes Care*, 1996, 19(8):887–891; Indolfi C. et al., *Am. Heart J.*, 1996, 132(3):542–549; Kondo, C. et al., *J. Nucl. Cardiol.*, 1996, 3(1):30–36; Chen S. L. et al., 1995, *Nucl. Med. Commun.* 16(5):336–343; Nozaki T. et al., 1995, *J. Nucl. Med.* 36(3):518–524). The fatty acid analogs frequently used include $^{123}$I-BMIPP and β-methyl[1-$^{14}$C]heptadecanoic acid and the methods of detection include positron emission tomography (PET) or single-proton-emission computed tomography (SPECT) (Franken, P. R. et al., *Acta Cardiol.*, 1996, 51(6):501–514; Knuuti M. J. et al., *J. Mol. Cell. Cardiol.*, 1995, 27(7):1359–1367; Nozaki T. et al., 1995, *J. Nucl. Med.* 36(3):518–524). These methods are relatively complex and costly because of the equipment required for testing. Thus, there is a need for a simple test for determining FFA in serum to reliable diagnosis of cardiac ischemia.

Drugs for lowering plasma levels of FFA or treating ischemic conditions are known (U.S. Pat. No. 5,589,467; U.S. Pat. No. 5,484,774; U.S. Pat. No. 5,430,027; U.S. Pat. No. 5,032,583). Drugs with such activities are potentially useful for treating hyperlipidemias, brain ischemia and cardiovascular disorders such as cardiac ischemia, cardiac arrhythmias, angina, hypertension and heart failure. Thus, there is a need for an assay for determining the efficacy of known drugs for lowering levels of serum FFA in a patient and for discovery of drugs with this property.

SUMMARY OF THE INVENTION

The present invention is a relatively simple method of detecting $FAA_u$ levels in serum that are associated with and diagnostic of cardiac ischemic conditions. The present invention is useful as a diagnostic tool for detecting cardiac ischemia, alone or in conjunction with other diagnostic determinations. It is also useful for monitoring the efficacy of treatments of cardiac disorders and for discovery of new agents that modulate serum levels of FFA.

According to the invention, there is provided a method of detecting cardiac ischemia in a mammal, comprising the steps of providing a serum sample obtained from the mammal, mixing the serum sample with an aqueous solution and with a reagent comprising a fatty acid binding protein labeled with a fluorescent moiety, wherein the reagent exhibits a first fluorescence in an aqueous solution and a measurably different second fluorescence in an aqueous solution when the fatty acid binding protein is bound to a free fatty acid, wherein the free fatty acid is unbound to serum albumin, measuring the second fluorescence after the serum sample is mixed with the aqueous solution and the reagent to determine a concentration of the free fatty acid in the serum sample, and determining whether the concentration of the free fatty acid in the serum sample is indicative of cardiac ischemia. In one embodiment, the providing step comprises providing a serum sample from a human. In another embodiment, the measuring step of the second fluorescence is performed at a wavelength that differs from a wavelength at which the reagent exhibits the first fluorescence. Preferably, the wavelength for measuring the second fluorescence is about 430 nm to about 450 nm, and the wavelength at which the reagent exhibits the first fluorescence is about 500 nm to about 550 nm. In one embodiment of the method, the determining step comprises determining that the concentration of the free fatty acid unbound to serum albumin in the serum sample is significantly higher than a concentration of free fatty acid unbound to serum albumin in serum of a control population that does not have cardiac ischemia. In another embodiment, the determining step comprises determining that the concentration of the free fatty acid unbound to serum albumin in the serum sample is about two standard deviations greater than an average concentration of free fatty acid unbound to serum albumin in serum of a control population that does not have cardiac ischemia. In a preferred embodiment, the determining step further comprises determining a degree of cardiac ischemia by determining that the concentration of the free fatty acid unbound to serum albumin in the serum sample is at least about two-fold greater than an average concentration of free fatty acid unbound to serum albumin in serum of the control population. In one embodiment, the determining step comprises determining that the concentration of the free fatty acid unbound to serum albumin in the serum sample is at least about 12 nM. Another embodiment of the method further comprises the steps of measuring total free fatty acid and albumin in the serum sample, and determining a ratio of the total free fatty acid and the albumin. In another embodiment, the reagent in the mixing and measuring steps is a fatty acid binding protein labeled with a fluorescent moiety, the fatty acid binding protein is a rat intestinal fatty acid binding protein, a human adipocyte fatty acid binding protein, or a human heart fatty acid binding protein, and the fluorescent moiety is acrylodan, danzyl aziridine, 4-[N-[(2-iodoacetoxy)ethyl]-N-methylamino]-7-nitrobenz-2-oxa-1,3-diazole ester (IANBDE), or 4-[N-[(2-iodoacetoxy)ethyl]-N-methylamino]- 7-nitrobenz-2-oxa-1,3-diazole (IANBDA). In a preferred embodiment, the reagent in the mixing and measuring steps is a fatty acid binding protein labeled with acrylodan, the fatty acid binding protein is a mutant protein comprising a rat intestinal fatty acid binding protein having a cysteine at residue 27, 81, 82, or 84, or an alanine at residue 72, or a human heart fatty acid binding protein having a lysine at residue 27. In another preferred embodiment, the reagent in the mixing and measuring steps is a rat intestinal fatty acid binding protein labeled with acrylodan. In another embodiment, the reagent in the mixing and measuring steps is a rat intestinal fatty acid binding protein labeled with a fluorescent moiety, wherein the fatty acid binding protein comprises a site-specific mutant in which at least one amino acid residue has been altered. Preferably, the reagent is a rat intestinal fatty acid binding protein labeled with acrylodan and having an alanine at residue 72.

DETAILED DESCRIPTION OF THE PREFERRED EMBODIMENT

Figure 1:
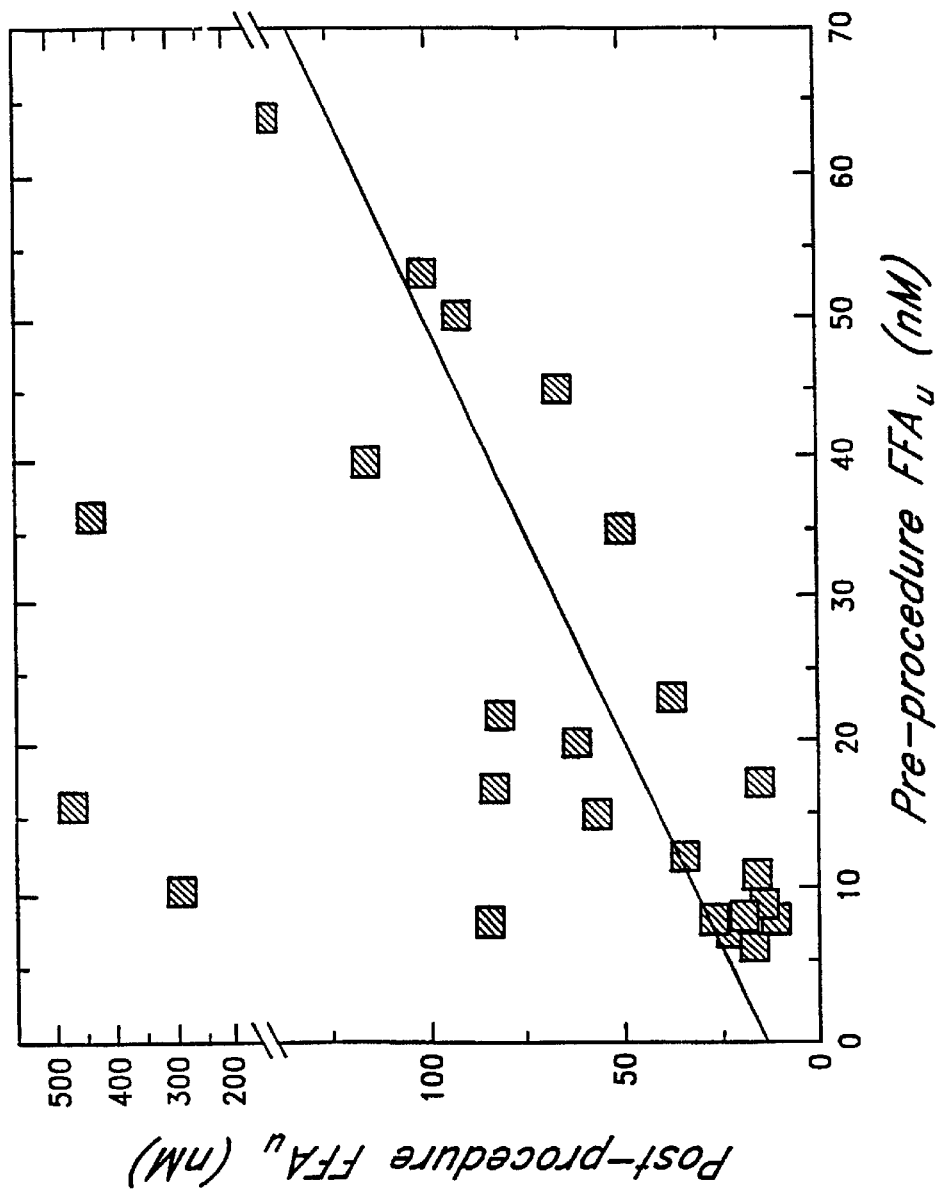
FIG. 1 is a graph showing a correlation between the serum levels of free fatty acid ($FAA_u$) before (pre-procedure, on the X-axis) and after (post-procedure, on the Y-axis) percutaneous transluminal coronary angioplasty, with a linear fit (shown by the diagonal line) that yields a positive correlation coefficient of 0.8 when the three highest values (greater than 250 nM) are excluded.

The present invention uses a fluorescently-labeled fatty acid binding protein (FABP) to measure an increased amount of $FAA_u$ in serum or plasma associated with cardiac ischemia by quantitatively detecting a shift in fluorescence associated with binding of a $FFA_u$ molecule to the fluorescently-labeled FABP. This invention utilizes the method substantially as described in U.S. Pat. No. 5,470,714. A variety of FABP and fluorescent labels can be used in detecting levels of serum or plasma $FAA_u$ indicative of cardiac ischemia. These include, for example, rat intestinal FABP (I-FABP), human adipocyte FABP (A-FABP) and human heart FABP (H-FABP). Site-specific mutant forms of these FABP, in which one or more amino acid residues have been altered (inserted, deleted and/or substituted) are also useful in the method and include, for example, substitutions of Cys in I-FABP at positions 27, 81, 82, 84, an Ala substitution at residue 72 of I-FABP, and a Lys substitution at residue 27 of H-FABP. The FABP molecules may be fluorescently-labeled using a variety of known labels including, for example, acrylodan, danzyl aziridine, 4-[N-[(2-iodoacetoxy)ethyl]-N-methylamino]-7-nitrobenz-2-oxa-1,3-diazole ester (IANBDE), and 4-[N-[(2-iodoacetoxy)ethyl]-N-methylamino]-7-nitrobenz-2-oxa-1,3-diazole (IANBDA). The fluorescently-labeled FABP used to produce the data reported herein was acrylodan-derivatized recombinant rat intestinal fatty acid binding protein (referred to as "ADIFAB") or acrylodan-derivatized recombinant rat intestinal fatty acid binding protein that has a Ala substitution at residue 72 (referred to as "ADIFAB2" and described in Richieri, G. V. et al., *J. Biol. Chem.*, 1996, 271:31068–31074). These were derivatized with acrylodan using known methods substantially as previously described (Richieri, G. V. et al., *J. Biol. Chem.*, 1992, 267:23495–23501), and ADIFAB is commercially available (Molecular Probes, Eugene, Oreg.). It will be understood that those skilled in the art can readily substitute other fluorescently-labeled FABP in the assay to provide substantially the same results for detecting ischemic-associated levels of serum or plasma $FAA_u$.

The diagnostic method of the present invention is based on the discovery that patients experiencing cardiac ischemia have elevated levels of $FFA_u$ in their serum compared to normal levels of serum $FFA_u$ in healthy individuals. These findings were based on determinations of serum $FAA_u$ levels in twenty-two patients who were undergoing percutaneous transluminal coronary angioplasty (PTCA), a controlled situation where ischemia occurs during balloon inflation. Serum $FFA_u$ levels were determined 5 min before ("pre-PTCA") and 30 min after ("post-PTCA") the PTCA procedure. In all patients tested, the post-PTCA serum $FAA_u$ levels were significantly higher than the pre-PTCA levels and significantly higher than serum $FAA_u$ levels in healthy individuals who did not undergo the PTCA procedure. The pre-PTCA serum $FFA_u$ levels of the cardiac patients were also elevated compared to healthy subjects. These results show that serum or plasma $FFA_u$ levels are increased in cardiac ischemic conditions (either cardiac ischemia related to coronary disease or angioplasty-induced ischemia) and, thus, detection of elevated levels of serum or plasma $FFA_u$ can be used for diagnosis of ischemic conditions in humans.

Diagnosis of cardiac ischemia by detection of elevated levels of serum or plasma $FAA_u$ was confirmed by results obtained with two other sets of cardiac patients. In one group of patients admitted to an emergency medical facility with chest pains, $FAA_u$ levels in serum were about six-fold higher than normal levels in individuals who were subsequently diagnosed as having experienced at least one ischemic event. In another group of patients who were given a treadmill exercise stress test and monitored for ischemia with ECG and echocardiography, the increased $FAA_u$ levels in serum shortly after completion of the stress test correlated well with ischemia detected by echocardiography, and more reliably than by ECG. Moreover, elevated levels of serum $FFA_u$ were detected in ischemic patients before the stress test was given, thus providing a diagnostic measurement of cardiac ischemia even in the absence of exercise stress.

Quantitative detection of levels of serum $FAA_u$ that are elevated over serum $FAA_u$ levels found in normal healthy individuals can be used to diagnose cardiac ischemic conditions, with or without increased ischemic stress induced by angioplasty or exercise. Independent of the origin of the ischemic event, cardiac ischemia is detected by levels of serum $FAA_u$ that equal or exceed the average normal serum $FAA_u$ level in normal controls (7.5±2.5 nM) plus about two standard deviations. That is, cardiac ischemia can be diagnosed by detecting levels of serum $FAA_u$ that are about or exceed 12 nM. Elevated levels of serum $FAA_u$ diagnostic of cardiac ischemia may be considerably higher depending on the nature of the ischemic event. That is, acute events such as angioplasty-induced ischemia or myocardial infarction can produce serum $FAA_u$ levels that are considerably higher than 12 nM, up to about sixty-fold over normal levels are diagnostic of ischemia. Cardiac ischemia can be diagnosed without or with exercise-stress induced ischemia by detecting levels of serum $FAA_u$ that are elevated to about two standard deviations of the serum $FAA_u$ levels in a relevant normal population, extending up to many-fold over the normal level (e.g., up to about fifty-fold or sixty-fold over normal).

Diagnosis of cardiac ischemia may also include measurement of total serum FFA and serum albumin and determining the ratio of total FFA to serum albumin (FFA/albumin ratio). Measuring albumin increases the accuracy of the cardiac ischemia diagnosis relative to the total serum FFA alone because the FFA/albumin ratio takes into account albumin values which may vary about 20% between individuals and because $FAA_u$ values tend to increase exponentially with the FFA/albumin ratio. Total serum FFA and total serum albumin can be determine readily using well-known procedures such as those commercially available using a nonesterified fatty acid C assay (NEFA C, from WAKO Pure Chemical Ind., Osaka, Japan) or the Albumin Reagent (BCG) Kit (from Sigma Diagnostics, St. Louis, Mo.). This measurement, however, is time-consuming (about 1 hr) and only indirectly measures the $FFA_u$ level.

For the results presented below, the assay was performed substantially as described in U.S. Pat. No. 5,470,714. Patients who participated in the studies reported herein gave their informed consent.

The assay for determination of $FFA_u$ levels in the serum measures the intensity of a shift in fluorescence from a first wavelength, at which the derivatized FABP fluoresces when no FFA is bound, to a second wavelength, at which the derivatized FABP fluoresces when a molecule of FFA is bound, and the concentration of $FFA_u$ is then determined from the ratio ("R" value) of the two intensities of fluorescence wavelengths as described in U.S. Pat. No. 5,470,714 and Richieri, G. V. & Kleinfeld, A. M., *J. Lipid Res.*, 1995, 36:229–240. Briefly, the ratio is calculated using the following formula:

$$R = \frac{[ADIFAB_b] \cdot I_b(1) + [ADIFAB_u] \cdot I_u(1)}{[ADIFAB_b] \cdot I_b(2) + [ADIFAB_u] \cdot I_u(2)}$$

wherein, $[ADIFAB_b]$ and $[ADIFAB_u]$ are the concentrations of bound and unbound ADIFAB, respectively; $I_b(1)$ and $I_u(1)$ are the specific fluorescence intensities of bound and unbound ADIFAB, respectively, at wavelength "1"; and $I_b(2)$ and $I_u(2)$ are the specific fluorescence intensities of bound and unbound ADIFAB, respectively, at wavelength "2". For ADIFAB, wavelength "1" is 505 nm and wavelength "2" is 432 nm.

Measurements of fluorescence intensities for the results presented herein were obtained using standard techniques (e.g., as described in U.S. Pat. No. 5,470,714 and Richieri, G. V. & Kleinfeld, A. M., *J. Lipid Res.*, 1995, 36:229–240) and fluorometer (SLM500, SLM4800 or SLM8000, Spectronics Instruments, Inc., Rochester, N.Y.). It will be understood by those skilled in the art that other fluorometer and standard measurement methods may be used to yield equivalent results. The reliability of these techniques to quantitatively measure $FAA_u$ has been demonstrated by showing that controlled mixtures (e.g., 1:1 binary mixture of oleate and arachidonate, and 11:27:41:21 quaternary mixture of stearate, palmitate, oleate and linoleate) of known concentrations of $FAA_u$, measured and determined by this method, provided a linear fit when the measured $FAA_u$ concentration was compared to the added $FAA_u$ concentration in the mixtures (Richieri, G. V. & Kleinfeld, A. M., *J. Lipid Res.*, 1995, 36:229–240).

Briefly the $FAA_u$ assay and determinations were performed as follows. Serum samples were diluted 100-fold in buffer (20 mM N-2-hydroxyethyl-piperazine-N'-2-ethane sulfonic acid (HEPES), 150 mM NaCl, 5 mM KCl and 1 mM $Na_2HPO_4$, adjusted to pH 7.4), yielding a serum albumin concentration of about 6 $\mu$M. A solution of 6 $\mu$M fatty acid-free human albumin plus 0.5 $\mu$M ADIFAB was the negative control. For each donor, two aliquots of serum were prepared: one "background" or "blank" sample of 1% serum, and one "experimental" sample of 1% serum plus 0.5 $\mu$M ADIFAB. The negative control, blank and experimental samples were incubated at 37° C. for 30 min and R values measurements were made within 2 min of each sample for a particular donor (to minimize the slow R value increase of 0.01 hr).

For each sample, multiple measurements of pairs of intensities were collected at 432 nm and 505 nm and, after substraction of the intensities of the blank sample, the R values were determined. At least two separate measurements were done on different days for each serum sample and the mean values and standard deviations of $FFA_u$ concentrations were determined. To determine the probabilities of a difference between sets of measures, differences in means were evaluated using Student's t test, where a p value of less than 0.05 was considered significant.

The efficacy of this method for diagnosis of cardiac ischemia is demonstrated by the following examples that describe clinical trials. In the first study, $FFA_u$ levels were determined under conditions of controlled ischemia induced by percutaneous transluminal coronary angioplasty (PTCA), where $FAA_u$ levels were determined before and after the procedure. This study showed that elevated $FAA_u$ levels correlated with cardiac ischemia. In the second study, serum $FAA_u$ levels were determined for patients who were admitted to an emergency medical facility with chest pains, who were subsequently diagnosed as having at least one cardiac ischemic event leading to admission. This study showed that serum $FAA_u$ levels in cardiac ischemia patients were significantly higher than those of normal healthy individuals. In the third study, $FAA_u$ measurements were made for patients before and after undergoing treadmill exercise stress testing, and these results were correlated with ECG and echocardiography results obtained from the same patients. This study showed that $FFA_u$ levels correlated well with the patient's echocardiograms and were a better measure of ischemia than ECG.

For comparison to normal $FAA_u$ levels, the results of these studies were compared to previously determined for serum $FFA_u$ concentrations determined from 283 serum samples from normal healthy donors (Richieri, G. V. & Kleinfeld, A. M., *J. Lipid Res.*, 1995, 36:229–240). The mean value of serum FFA, concentration for normal individuals was determined to be 7.5±2.5 nM, with no significant differences noted in subpopulations divided by age or gender. The reproducibility of the measurements was demonstrated by testing multiple samples collected from the same individuals on separate occasions, yielding an average standard deviation of 1A nM, consistent with the intrinsic measurement uncertainty for normal donors.

The following examples illustrate some of the preferred embodiments of the invention.

EXAMPLE 1

Elevated Serum FFA, Levels Following Coronary Angioplasty

In this clinical trial, 22 patients (8 women, 14 men, ranging 43 to 85 yr old) were tested for serum $FAA_u$ levels before and after percutaneous transluminal coronary angioplasty (PTCA), where the angioplasty procedure induced temporary cardiac ischemia. All of the patients, who provided informed consent to participate in this study, had overt coronary artery disease and were scheduled to undergo PTCA and rotational atherectomy as treatment using standard clinical procedures. Twelve of the patients had had an earlier myocardial infarction and 20 had stable or unstable angina. All rotational atherectomy procedures were followed by adjunctive PTCA, using standard clinical procedures in which specific events (e.g., number and duration of balloon inflations) were determined by the treating physician. For the 20 patients treated with PTCA, the number of balloon inflations ranged from one to 20, the duration of inflation ranged from 30 sec to 5 min, and the total time for the procedure ranged from 42 to 95 min.

Blood samples for $FAA_u$ level determinations were collected from the side port of a femoral venous (central) cannula and an antecubital (peripheral) vein at initiation of catheterization and 30 min after the last balloon inflation. Each patient received a 10,000 U bolus of heparin after the initial blood sample was obtained and sufficient heparin was maintained during the angioplasty procedure to maintain clotting time activation at 300 sec. The 2 ml to 3 ml blood samples were centrifuged (5 min at 5,000 rpm) immediately after collection to pellet cells, the serum was removed and frozen, and the frozen serum samples were later tested for FFA concentrations. The serum $FAA_u$ levels for central and peripheral samples were equivalent (p>0.50).

ECG monitoring was performed during the angioplasty procedure by simultaneously recording two leads: a pericardial lead in the left thorax, and a standard limb lead (VF for right coronary artery angioplasty, VL for left coronary artery angioplasty). The ECG was monitored continuously during the procedure and ST segment shifting of greater than 1 mm were considered significant.

Table 1 presents the average $FAA_u$ values for each of the patients.

TABLE 1

| Patient No. | ST Change | $FFA_u$ (nM) Pre-PTCA | $FFA_u$ (nM) Post-PTCA | Ratio: Post-PTCA/Pre-PTCA |
|---|---|---|---|---|
| 1 | + | 8 | 84 | 10.5 |
| 2 | 0 | 17 | 83 | 4.9 |
| 3 | 0 | 9 | 14 | 1.6 |
| 4 | + | 40 | 115 | 2.9 |
| 5 | 0 | 6 | 17 | 2.8 |
| 6 | 0 | 7 | 17 | 2.4 |
| 7 | + | 53 | 99 | 1.9 |
| 8 | + | 9 | 37 | 4.1 |
| 9 | + | 64 | 140 | 2.2 |
| 10 | 0 | 15 | 56 | 3.7 |
| 11 | 0 | 22 | 81 | 3.7 |
| 12 | 0 | 50 | 90 | 1.8 |
| 13 | 0 | 8 | 18 | 2.3 |
| 14 | + | 45 | 64 | 1.4 |
| 15 | + | 11 | 16 | 1.5 |
| 16 | ± | 16 | 471 | 29.4 |
| 17 | + | 10 | 294 | 29.4 |
| 18 | + | 8 | 27 | 3.4 |
| 19 | ± | 7 | 22 | 3.1 |
| 20 | + | 36 | 440 | 12.2 |
| 21 | 0 | 35 | 49 | 1.4 |
| 22 | + | 12 | 34 | 2.8 |
| Mean: | | 22 ± 18 | 103 ± 130 | 4.7 |

The average post-angioplasty $FAA_u$ value (103 nM) was significantly (p<0.005) greater than the average pre-angioplasty $FAA_u$ value (22 nM). In addition, the distribution of the pre-angioplasty and post-angioplasty $FAA_u$ levels in these patients differ considerably from the distribution of values in the normal population. Although some of the pre-angioplasty levels were within one or two standard deviations of the mean $FAA_u$ value for normal individuals (7.5±2.5 nM), eleven of the twenty-two patients in this study had significantly higher $FFA_u$ concentrations.

The $FAA_u$ concentrations in the serum also correlated with the ECG responses seen in the individual patients. Referring to Table 1, the ECG changes are shown for each of the patients, where "+" indicates ST segment shifts of greater than 1 mm, "0" indicates no ST segment shifts or shifts less than 1 mm, and "±" indicates ambiguous results for two patients. The pre-PTCA and post-PTCA levels of serum $FAA_u$ were highly correlated with electrocardiographic changes. Both pre-PTCA and post-PTCA levels of serum $FAA_u$ were lower (19±15 nM and 47±32 nM, respectively) in patients who had no ECG change compared to the pre-PTCA and post-PTCA levels of serum $FAA_u$ (27±21 nM and 123±131 nM, respectively) for those patients who exhibited significant ECG changes. Moreover, large increases in serum $FAA_u$ values (mean=28 nM) occurred even in patients without significant ECG changes. Thus, the $FAA_u$ values are a more sensitive measure of cardiac ischemia than ECG changes.

As shown in Table 2, the ratios of the pre-PTCA $FAA_u$ level to the $FAA_u$ value for normal individuals (calculated using 7.5 nM for normal), was generally greater than one, with an average increase of about three-fold, ranging up to about nine-fold over normal. When the same calculations were done for all twenty-two patients comparing their post-PCTA $FAA_u$ level to the $FAA_u$ value for normal individuals who are not ischemic, the levels were again greater, averaging about fourteen-fold over normal levels and ranging up to about 63-fold over normal levels. Three patients' post-angioplasty $FAA_u$ values of 300 nM or more were at least about 40-fold greater than normal

TABLE 2

| Patient No. | Ratio Pre-PTCA/normal | Ratio Post-PTCA/normal |
|---|---|---|
| 1 | 1.07 | 11.2 |
| 2 | 2.27 | 11.1 |
| 3 | 1.20 | 1.87 |
| 4 | 5.30 | 15.30 |
| 5 | 0.80 | 2.27 |
| 6 | 0.90 | 2.27 |
| 7 | 7.07 | 13.20 |
| 8 | 1.20 | 4.93 |
| 9 | 8.53 | 18.67 |
| 10 | 2.00 | 7.47 |
| 11 | 2.93 | 10.80 |
| 12 | 6.67 | 12.00 |
| 13 | 1.07 | 2.40 |
| 14 | 6.00 | 8.53 |
| 15 | 1.47 | 2.13 |
| 16 | 2.13 | 62.80 |
| 17 | 1.33 | 39.20 |
| 18 | 1.07 | 3.60 |
| 19 | 0.90 | 2.93 |
| 20 | 4.80 | 58.67 |
| 21 | 4.67 | 6.53 |
| 22 | 1.6 | 4.53 |

Referring to FIG. 1, the pre-angioplasty $FAA_u$ levels were correlated with the post-angioplasty $FFA_u$ levels for these patients to determine if the pre-angioplasty levels reflect the disease state of the patients. Generally, the pre-angioplasty $FAA_u$ levels were predictive of the magnitude of the post-angioplasty $FFA_u$ levels. Except for the patients with the highest post-angioplasty $FAA_u$ levels of greater than 250 nM, the post-angioplasty $FAA_u$ levels were linearly correlated with the pre-angioplasty levels. These results show that the $FAA_u$ levels in individuals with cardiac ischemia resulting from coronary disease are diagnostic of the disease state of the individual. The increased ischemia induced by the angioplasty procedure was also measurable by the post-angioplasty $FAA_u$ levels in the serum.

For a subset of seven patients in this study, total serum FFA and albumin were also measured and the FFA/albumin ratios were determined. These patients ranged from $FAA_u$ levels about normal (8 nM for patient 13) to the highest levels observed in this group (550 nM for patient 16). As shown in Table 3, the $FAA_u$ levels were well correlated with the serum $FAA_u$ levels, similar to the results seen with samples from normal individuals (Richieri, G. V. & Kleinfeld, A. M., J. Lipid Res., 1995, 36:229–240). Thus, measurements of the total serum FFA and albumin serve as additional parameters, in addition to serum $FAA_u$ levels, for diagnosis of cardiac ischemia.

TABLE 3

| Patient No. | Total FFA (nM) | Albumin (mM) | FFA/Albumin | FFAu (nM) |
|---|---|---|---|---|
| 13 | 0.5 | 0.602 | 0.8 | 8 |
| 3 | 0.6 | 0.563 | 1.1 | 11 |
| 18 | 1.26 | 0.407 | 3.1 | 26 |
| 9 | 2.15 | 0.468 | 4.6 | 61 |
| 4 | 1.94 | 0.383 | 5.1 | 115 |
| 20 | 3.64 | 0.483 | 7.5 | 470 |
| 16 | 2.8 | 0.393 | 7.1 | 550 |

EXAMPLE 2

Elevated Serum $FFA_u$ Levels in Cardiac Patients Admitted for Emergency Care

Figure 2:
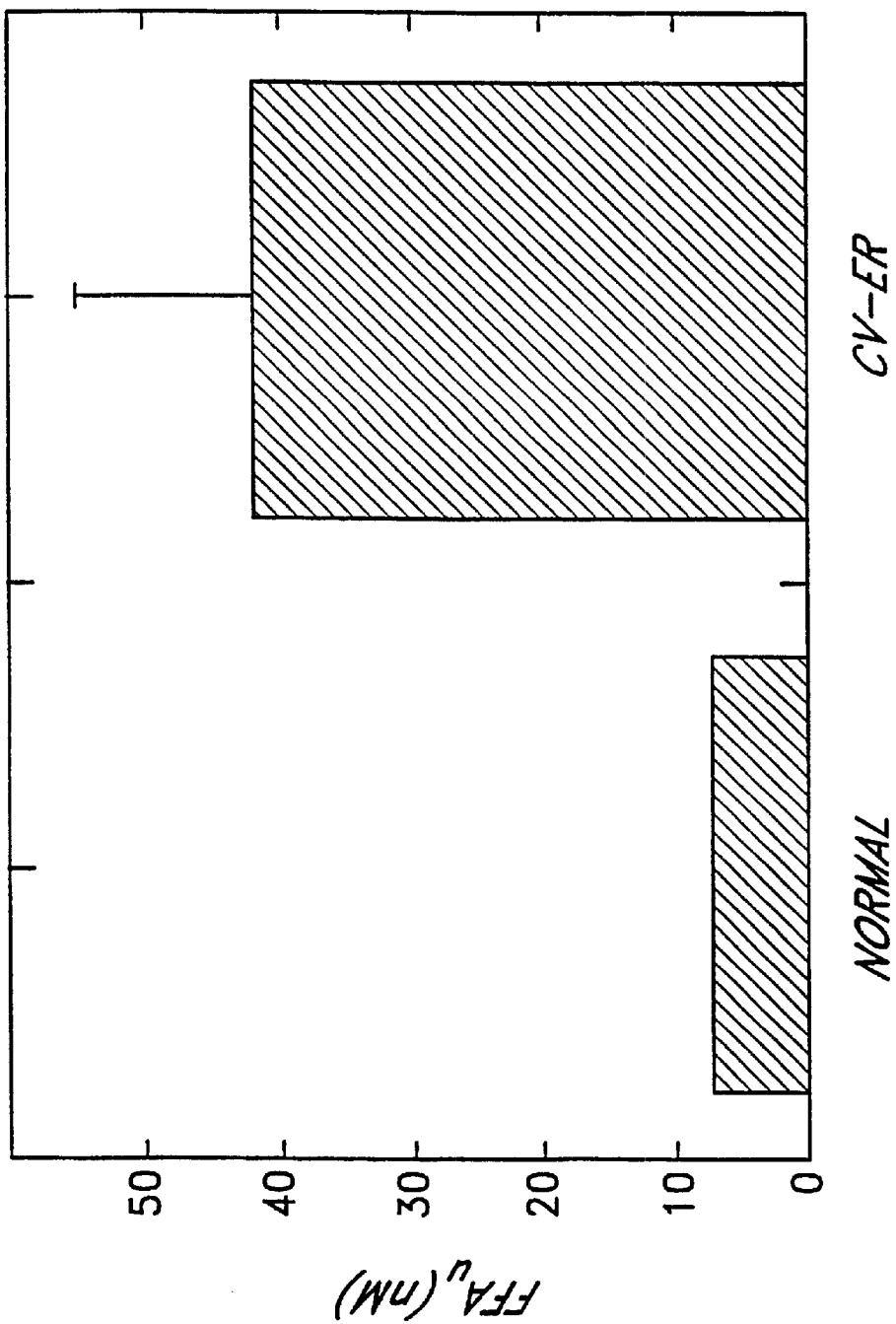
FIG. 2 is a bar graph showing the average $FAA_u$ (nM) levels of about 30 patients admitted to an emergency medical facility with chest pains who were subsequently diagnosed as ischemic ("CV-ER") and the average $FFA_U$ levels (7.5±2.5 nM) of about 300 normal control subjects having no cardiovascular disease symptoms ("Normal").

In this study, blood samples were obtained from 31 patients, aged 58 yr to 90 yr, who were admitted to an emergency medical facility with chest pains. These patients were all subsequently diagnoses as having at least one ischemic event by the treating physician (e.g., angina, myocardial infarct). The blood samples (about 5 ml) were collected using standard venous collection procedures from a limb; the samples were treated substantially as described in Example 1 and the serum $FAA_u$ concentrations were determined using ADIFAB as described above. The serum $FAA_u$ concentrations of these patients were averaged (42±12 nM) and compared to the average serum $FAA_u$ concentrations of normal healthy individuals (7.5±2.5 nM). Referring to FIG. 2, it is clear that the patients suffering from cardiac ischemia ("CV-ER") had significantly higher levels of serum $FAA_u$ than seen in non-ischemic normal controls, averaging about 5.5-fold higher than seen in the healthy controls. Thus, determination of serum $FAA_u$ concentrations is diagnostic of cardiac ischemia and can be used to confirm or disaffirm other symptoms (e.g., chest pains) that may or may not be indicative of cardiac ischemia.

EXAMPLE 3

Elevated Serum $FFA_u$ Levels Correlate with Exercise-induced Cardiac Ischemia

In this study, eleven patients undergoing treadmill exercise stress testing were assayed for two commonly used diagnostic measurements, ECG and echocardiogram, and their serum $FAA_u$ levels were determined before and after the stress testing. Blood samples were collected from a limb vein using standard procedures at a time just before the treadmill test, and at 5 min, 30 min and 24 hr after completion of the treadmill test. The samples were treated and tested for determination of $FAA_u$ levels substantially as described above except that the FABP test reagent was an acrylodan-derivatized recombinant rat intestinal fatty acid binding protein having an Ala substitution at residue 72 (referred to as "ADIFAB2"). This detector compound is a relatively high affinity variant of the ADIFAB detector and therefore it has greater sensitivity to the low concentrations of $FAA_u$ found in serum than ADIFAB, it is less prone to drift (fluctuations in measurements over time) than ADIFAB, and because its emissions occur at longer wavelengths (550 nm for unbound ADIFAB2, and 450 nm for FFA-bound ADIFAB2) it is less sensitive to interference effects by hemoglobin.

Figure 3:
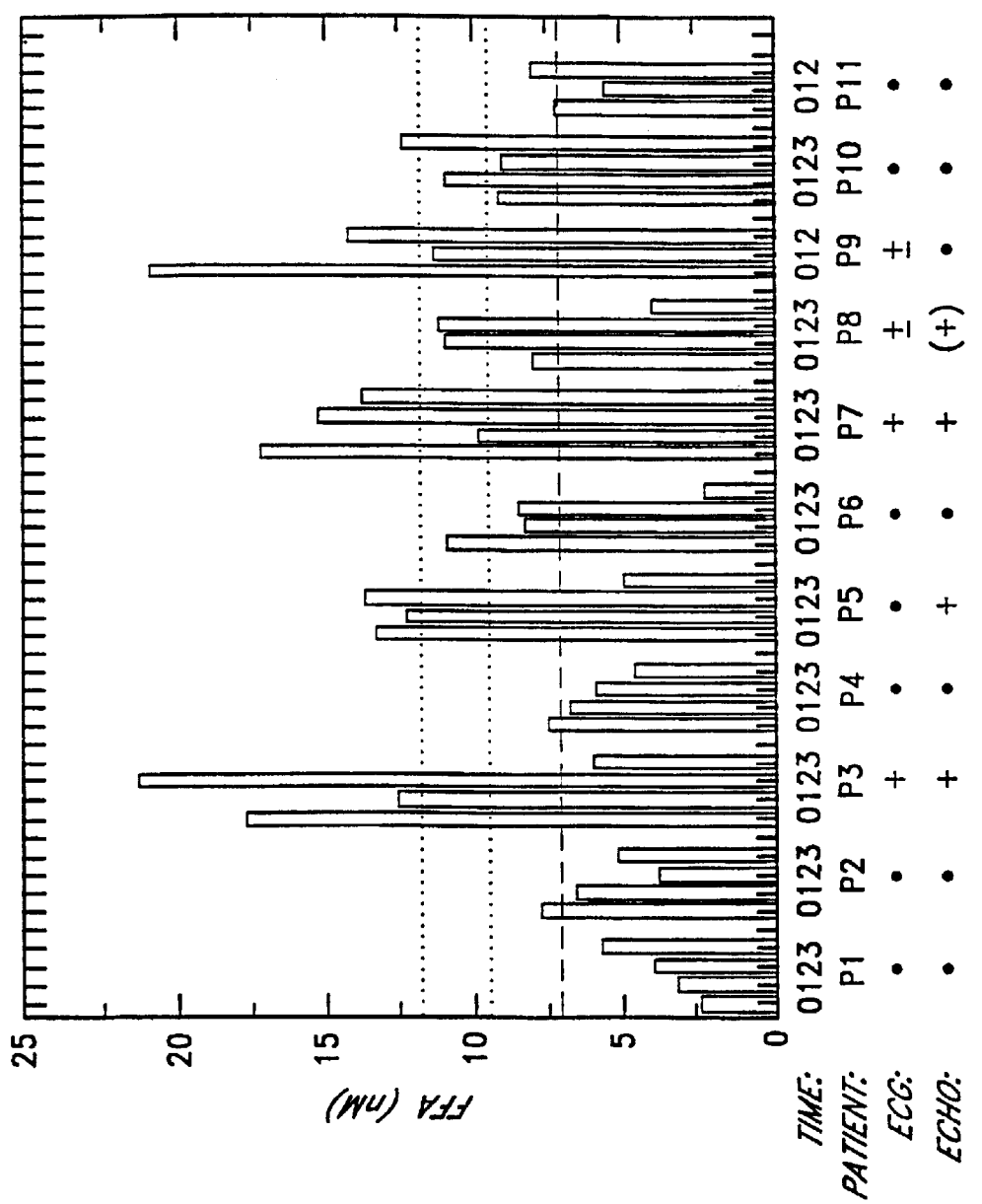
FIG. 3 is a bar graph showing the $FAA_u$ (nM) levels in serum obtained from eleven patients ("P1" to "P11") before exercise (time: 0), 5 min (time: 1), 30 min (time: 2) and 24 hr (time: 3) after the end of a treadmill exercise test, compared with the results of an electrocardiogram (ECG) and echocardiogram (ECHO) for each of the patients in which "−" indicates negative results for ischemia, "+" indicates positive results for ischemia, "(+)" indicates mild ischemia detected, and "±" indicates non-diagnostic baseline fluctuations making ischemia results uninterpretable. Patient 9 presented with chest pain and had previously had a myocardial infarction. The dashed line across the graph at about 7 nM represents the normal control level of $FAA_u$; the dashed line at about 9 nM represents one standard deviation and the dashed line at about 12 nM represents two standard deviations from the normal control level of $FFA_u$.

As shown in FIG. 3, six of the patients showed negative results for both ECG and echocardiograms during the treadmill testing (patients P1, P2, P4, P6, P10 and P11), two patients showed positive results for both echocardiograms during treadmill testing (patients P3 and P7), and three patients showed mixed or ambiguous results for ECG and echocardiograms (patients P5, P8 and P9). For patients P8 and P9, the ECG test results were non-diagnostic because baseline fluctuations made the ischemia results uninterpretable.

For the majority of the patients (P2 to P11), at least one $FAA_u$ measurement exceeded the normal control mean level indicated by the dashed horizontal line on FIG. 3 at about 7.5 nM. Seven of the patients (P3, P5, P6, P7, P8, P9 and P10) had one or more measurements of $FAA_u$ concentration that exceeded the normal control level plus one standard deviations (indicated by the dashed line at about 9 nM), and these same patients had at least one $FAA_u$ level. that approached or exceeded the normal control level plus two standard deviations (indicated by the dashed line at about 12.5 nM). For all of the patients with serum $FAA_u$ levels significantly above normal, except P7 and P10, the serum $FAA_u$ levels decreased by 24 hr after the treadmill exercise test was completed. For patients P3, P5, P7 and P9, who exhibited significantly elevated serum FAAlevels just before the treadmill testing began, at least one measurement of serum $FAA_u$ after treadmill testing was also significantly higher than normal (e.g., at 5 min and/or 30 min after completion of the test). Importantly, for patients P3, P5 and P7, who had positive ECG and/or echocardiogram results during exercise stress testing, their ischemia was detected by serum $FAA_u$ before exercise stress. Patients with positive results for ischemia by echocardiography (P3, P5, P7), generally showed serum $FAA_u$ levels indicative of cardiac ischemia before and after completing treadmill testing (5 min and/or 30 min after the test). One patient (P8) who exhibited mild ischemia as detected by echocardiography also showed elevated serum $FAA_u$ levels at 5 min and 30 min after treadmill exercise stress, compared to normal levels before and 24 hr after completion of the treadmill test. Some patients who tested negative or ambiguously for ischemia by ECG (P5, P8 and P9) had serum $FAA_u$ levels indicative of cardiac ischemia, showing that the $FAA_u$ levels are a more sensitive and for reliable indicator of cardiac ischemia than ECG, consistent with the angioplasty study results presented in Example 1.

These results show that elevated serum $FAA_u$ levels indicative of cardiac ischemia can be detected even in the absence of exercise stress.

It should be apparent from the foregoing discussion that various other derivatized FABP agents may be substituted in the method to give similar diagnostic results. Accordingly, the invention may be embodied in other specific forms. The examples represent illustrative preferred embodiments and are not restrictive on the scope of the invention, which is defined by the appended claims and their lawful equivalency.

What is claimed is:

1. A method of detecting stable or unstable angina in a mammal, comprising the steps of:

providing a serum or plasma sample obtained from said mammal;

mixing said mammalian serum or plasma sample with an aqueous solution and with a reagent comprising a fatty acid binding protein labeled with a fluorescent moiety, wherein said reagent exhibits a first fluorescence in an aqueous solution and a measurably different second fluorescence in an aqueous solution when said fatty acid binding protein is bound to a fatty acid;

measuring said second fluorescence after said mammalian serum or plasma sample is mixed with said aqueous solution and said reagent to determine a concentration of unbound free fatty acid in said serum or plasma sample;

comparing said concentration of said unbound free fatty acid in said mammalian serum or plasma sample to a concentration of unbound free fatty acid in serum or plasma of a control population that does not have stable or unstable angina; and determining whether said concentration of said unbound free fatty acid in said mammalian serum or plasma sample is indicative of stable or unstable angina.

2. The method of claim 1, wherein said providing step comprises providing a serum or plasma sample from a human.

3. The method of claim 1, wherein said measuring step of said second fluorescence is performed at a wavelength that differs from a wavelength at which said reagent exhibits said first fluorescence.

4. The method of claim 3, wherein said wavelength for measuring said second fluorescence is about 430 nm to about 450 nm, and wherein said wavelength at which said reagent exhibits said first fluorescence is about 500 nm to about 550 nm.

5. The method of claim 1, wherein said determining step comprises determining that said concentration of said unbound free fatty acid in said mammalian serum or plasma sample is at least about two standard deviations greater than an average concentration of unbound free fatty acid in serum or plasma of a control population that does not have stable or unstable angina.

6. The method of claim 5, wherein said determining step further comprises determining a degree of stable or unstable angina by determining that said concentration of said unbound free fatty acid in said mammalian serum or plasma sample is at least about two-fold greater than an average concentration of unbound free fatty acid in serum or plasma of said control population.

7. The method of claim 1, wherein said reagent in said mixing and measuring steps is a fatty acid binding protein labeled with acrylodan, wherein said fatty acid binding protein is a mutant protein comprising a rat intestinal fatty acid binding protein having a cysteine at residue 27, 81, 82, or 84, or an alanine at residue 72, or a human heart fatty acid binding protein having a lysine at residue 27.

8. The method of claim 7, wherein said reagent is a rat intestinal fatty acid binding protein labeled with acrylodan and having an alanine at residue 72.

* * * * *